United States Patent [19]

Lesser

[11] Patent Number: 4,832,978

[45] Date of Patent: May 23, 1989

[54] SIMULATED CONNECTIVE TISSUE FOR CONSTRUCTION OF MODELS AND PROSTHESES

[76] Inventor: Jary M. Lesser, 1300 Moursund, Houston, Tex. 77030

[21] Appl. No.: 42,257

[22] Filed: Apr. 24, 1987

[51] Int. Cl.$^4$ .............................................. B05D 1/14
[52] U.S. Cl. ...................................... 427/2; 427/203; 427/206; 428/86; 428/90; 428/15; 623/15
[58] Field of Search ........................... 427/203, 206, 2; 428/86, 90, 15; 623/15

[56] References Cited

U.S. PATENT DOCUMENTS

| | | | |
|---|---|---|---|
| 3,940,524 | 2/1976 | Hoppe et al. | 428/86 |
| 4,034,134 | 7/1977 | Gregorian et al. | 427/203 X |
| 4,142,929 | 3/1979 | Otomine | 427/206 X |
| 4,396,662 | 8/1983 | Higashiguchi | 427/206 |
| 4,570,627 | 2/1986 | MacConkey et al. | 428/40 X |
| 4,621,029 | 11/1986 | Kawaguchi | 428/60 X |

*Primary Examiner*—Shrive Beck
*Attorney, Agent, or Firm*—Pravel, Gambrell, Hewitt, Kimball & Krieger

[57] ABSTRACT

A cured emulsion of a polymerizable silicone compound and an inert paste such as petroleum jelly, liquid soap solution, or combination thereof forms a tough, elastic material that simulates the characteristics of connective tissue when used to join an outer skin layer to an understructure, and is useable in the production of models and prostheses. The silicone compound is preferably a mixture of a room temperature vulcanizable silicone rubber and a low viscosity silicone fluid. A high viscosity plasticizer, such as high viscosity silicone fluid, can be added to the emulsion to better simulate the characteristics of connective tissue. The emulsion is preferably joined to the outer skin layer by adhering fiber to the emulsion and coating the emulsion and fibers with the outer layer.

11 Claims, No Drawings

SIMULATED CONNECTIVE TISSUE FOR CONSTRUCTION OF MODELS AND PROSTHESES

FIELD OF THE INVENTION

This invention relates to the construction of models of animals and prostheses that simulate the characteristics of living tissue, more specifically, the characteristics of connective tissue.

BACKGROUND OF THE INVENTION

A wide variety of techniques are used to manufacture prostheses and models that have the feel and appearance of living tissue. Methods for manufacturing simulated skin which have the texture and appearance of animal or human skin are known in the art. However, models of animals or prostheses prepared from artificial skin often lack the feel of living tissue because the artificial skin is not connected to underlying structures in a manner that simulates the characteristics of connective tissue.

SUMMARY OF THE INVENTION

The present invention includes a composition that simulates the characteristics of connective tissue and a method of producing models and prostheses employing the composition to join an outer skin layer to underlying structures. The composition primarily consists of a cured emulsion of a polymerizable silicone compound and a viscous, inert substance such as petroleum jelly or liquid detergent. A preferred silicone compound is a combination of a room temperature vulcanizable silicone rubber and a low viscosity silicone fluid which cures to a porous gel when emulsified with an inert viscous paste such as petrolatum or concentrated liquid soap solution. A thin layer of the cured emulsion can be incorporated between the outer skin layer and the substructure of models and prostheses such that the skin layer moves with respect to the underlying structure. A preferred method of connecting the outer skin to the cured emulsion consists of adhering fibers to the cured emulsion and coating the cured emulsion with a liquid latex that bonds to the fibers.

DETAILED DESCRIPTION OF AN EMBODIMENT OF THE INVENTION

The following description details making of models of animals such a reptiles, but the process could be used to construct life-like human models and prostheses.

CONNECTIVE TISSUE GEL

The principal composition of the present invention is a cured emulsion of a polymerizable silicone compound and an inert nonsilicone paste and is hereafter referred to as the "connective tissue gel." This composition forms a loose, elastic, tough material which has the inert paste substance within small voids dispersed throughout the gelled silicone compound. When layered immediately under the outer skin layer of a model or prosthesis, the connective tissue gel will render the skin mobile and closely mimics the mobility of the skin of living animals. The outer skin of such a model can be moved over the understructure of the model or prosthesis which can be constructed to simulate bone, muscle, or other living tissue.

The silicone compounds preferably consist of long and short chain polymers having the following basic formula:

$$Si(CH_3)_2-O_n$$

although one or more of the methyl groups (CH3) in the chain can be replaced with hydrogen or other organic groups without substantially altering the physical properties. The present invention works well using commercially available silicone compounds, but is not limited to such commercial compounds.

Petroleum jelly, also known as petrolatum or mineral jelly, is one example of the inert paste component, and can be either a natural or a synthetic formulation as the important properties are that the material remain gelatinous at normal conditions for the model or prosthesis and from an emulsion when mixed with polymerizable silicone compounds. A concentrated liquid soap solution can serve the same function as the petroleum jelly. The mechanical, rather than chemical, properties of this pastelike substance permit it to be dispersed as an emulsion in the silicone gel. The paste must: (1) not react chemically with the silicone compounds: (2) contain a minimum of volatile solvents; (3) not itself be a silicone; and (4) be stable under normal conditions for use of the model or prosthesis. A variety of substances are believed to fit the limitations although liquid soap and petrolatums are the only examples of such compounds that have been actually used.

The polymerizable silicone compound is preferably emulsified with the paste and allowed to cure to form the elastic, tough material. A wide variety of silicone compounds could be used depending on the desired elasticity and strength of the connective tissue gel. A preferred composition that closely simulates the characteristics of connective tissue as will be described in more detail below is prepared by combining one volume of a room temperature vulcanizing silicone rubber such as Dow Corning RTV 732 Silastic 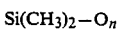 with about 4 to about 6 volumes, relative to the RTV 732, of a low viscosity silicone fluid such as Dow Corning 200 silicone fluid having a 5 centistoke viscosity. This silicone compound is preferably emulsified with an inert paste of about 1 to about 1.5 volumes, relative to the RTV 732, of petroleum jelly or about 1-6 volumes of a concentrated liquid dish soap or combinations thereof, and applied to models and prostheses in a partially cured or fully cured form as further described below. The rate of curing of the silicone compound is improved by adding about 2 drops of water per 15 cc of the silicone compound.

The plasticity of the silicone compound described above is improved by the addition of a high viscosity liquid after the initiation of polymerization. The high viscosity liquid is preferably a high viscosity silicone fluid such as Dow Corning 200 silicone fluid having a viscosity of 200 centistokes.

A highly preferred connective tissue gel has been produced by combining one volume of the Dow Corning RTV 732 Silastic ® with about 2 volumes of the Dow Corning 200 Silicone Fluid having 5 centistoke viscosity and allowing this mixture to polymerize thirty minutes at room temperature following the addition of about 2 drops of water per 15 cc of the mixture. After thirty minutes, about 2 more volumes of Dow Corning 200 Silicone Fluid having 5 centistokes viscosity is mixed thoroughly with the composition. Petroleum jelly is then mixed with the composition in an amount of from about 1 to about 1.5 volumes followed by the addition of about 0.5 to about 0.75 volumes of Dow Corning 200 Silicone Fluid having a viscosity of 200 centistoke and thorough mixing. A liquid dish soap such as Palmolive is then added in an amount of from about 1 to about 6 volumes, most preferably about 6 volumes, relative to the RTV 732, and thoroughly blended to form an emulsion. Better results are obtained if the liquid dish soap is gently heated prior to mixing so as to slightly increase the viscosity and reduce the water content of the dish soap.

MODEL CONSTRUCTION

The connective tissue gel described above has been used to construct models of animals having outer layers of skin that are moveable with respect to foam rubber understructures in a manner that closely resembles the characteristics of connective tissues. The connective tissue gel can be fully cured and applied to the model with adhesives or applied to the model in a partially cured form and allowed to cure on the model if curing results in sufficient adhesion of the connective tissue gel to the understructure.

PREPARATION OF UNDERSTRUCTURE

Foam rubber models of dinosaurs were used as the understructure for models constructed employing the present invention. The foam rubber structures were modified by the addition of skeletal components which could be felt beneath the moveable skin layer attached as described below. Skeletal components were formed by hollowing out portions of the foam rubber structure which were desired to have a more rigid material and filling the cavities with a mixture of 1 volume of Chemco ® mold builder liquid latex or equivalent material and 1 volume of talc or baby powder. After all the cavities are filled, the models are oven dried at about 135° F. for sixty to ninety minutes to cure the latex/talc mixture which has the texture of stiff cartilage when dried. For large skeletal members, the latex/talc mixture can be reinforced with slivers of wood or other materials.

Prior to attachment of the connective tissue gel and the outer skin layer, the foam rubber is sealed with a polymerizable silicone base adhesive to fill all the spaces in the foam. A preferred silicone base adhesive for sealing the foam is prepared by mixing 1 volume of Dow Corning RTV 732 Silastic ® with about 4 to about 6 volumes, preferably about 4 volumes, of Dow Corning 200 Silicone Fluid having a viscosity of 5 centistokes. The addition of four drops of water per 25 cc of the silicone base speeds polymerization. The exact composition of the silicone base preferably matches the composition of the silicone compound in the connective tissue gel to reduce diffusion of 5 centistoke silicone fluid. All foam rubber portions of the understructure of the model which are to be covered with the outer skin should be saturated with the silicone base. The silicone base is cured for at least 6 to 9 hours before addition of the connective tissue gel and outer skin.

PLACEMENT OF CONNECTIVE TISSUE GEL

Portions of the model which are desired to have an investment of connective tissue are then coated with a thin layer of the connective tissue gel which has been allowed to set for 30-60 minutes after formation of the emulsion. A preferred thickness for the layer is between about 0.1 milimeters and 0.2 milimeters. The partially cured emulsion is allowed to set for 5 to 10 additional minutes before cotton or other suitable fibers are applied to the sticky surface for reasons to be described below. The connective tissue gel can be formed into folds and wrinkles at this time if desired. The connective tissue gel is then allowed to cure for at least 6 hours before the addition of the outer skin layer.

Alternatively, the connective tissue gel can be prepared as above, and a thin layer poured onto a non-reactive surface, such as a disposable styrofoam plate, and allowed to age for at least 3 to 5 days to insure that the connective tissue gel is fully cured. Sections of the cured gel can then be cut and lightly stretched over the appropriate portions of the understructure of the model. The cut sections of the gel can be temporarily secured with toothpicks or other suitable means prior to the application of an adhesive. The preferred adhesive is the silicone base which can be blotted over and under the the connective tissue gel. After 30 to 90 minutes, fibers, such as cotton fibers, can be adhered to the silicone base on the outer surface of the connective tissue gel.

Portions of the model which are not covered with the connective tissue gel, but will be covered with the outer skin, are also coated with the fibers using the silicone base adhesive. The fibers are allowed to stand on the model for 1 to 2 hours and then loose fibers are carefully picked away to leave a light uniform fuzz that is tightly bonded on all surfaces that will receive the outer skin.

OUTER SKIN

A liquid latex such as Paratol ® or its equivalent is preferred to simulate a horny or leathery outer skin. The liquid latex is pigmented to the desired color, such as by the addition of food coloring, and is carefully painted over all fiber covered surfaces of the model. The liquid latex is then blotted to the desired shape and thickness and dusted with talc. The latex coating can then be imprinted with any appropriate design such as scales or cross-hatching with a knife blade, screen, or other suitable device. Other features can be added to the model as desired.

In certain cases where a horny or leathery outer layer is not desired, this outer latex skin may be omitted. Examples include prostheses simulating the texture of youthful human skin, or models of mammalian animals. In such cases, the outer skin is simply formed of silicone base, suitably pigmented, and perhaps reinforced with fibers.

After the outer skin dries, it can be pinched and moved over the understructure in a manner that simulates the characteristics of connective tissue although it still remains bonded to the understructure.

The preceding description of the present invention is not intended to limit the invention to the specific embodiments. Variations in composition, materials, and procedures that would be readily apparent to persons skilled in the art are intended to be included in the scope of the invention.

What is claimed is:

1. A method for connecting a surface layer to an understructure to simulate the characteristics of connective tissue, comprising the steps of:
  applying a thin layer of a partially cured emulsion of a polymerizable silicone compound and an inert paste to the understructure;

embedding fibers in the partially cured silicone compound;

coating the emulsion after curing of the silicone compound with a liquid outer layer that binds with the fibers upon drying; and drying the coated emulsion surface layer.

2. The method of claim 1, wherein the silicone compound is a mixture of a room temperature vulcanizing silicone rubber and a low viscosity silicone fluid.

3. The method of claim 2, wherein the emulsion further contains a high viscosity silicone fluid.

4. The method of claim 3, wherein the inert paste is selected from a group consisting of petrolatum, liquid detergent, and combinations thereof.

5. The method of claim 2, wherein the high viscosity silicone fluid, the inert paste, and about 2 to about 4 volumes of the low viscosity silicone fluid are added to a partially polymerized mixture of about 1 volume of silicone rubber and about 2 volumes of the low viscosity silicone fluid.

6. The method of claim 1, further comprising the step of constructing a skeletal member in the understructure from a mixture of latex and talc prior to application of the emulsion.

7. A method of connecting a surface layer to an understructure to simulate the characteristics of connective tissues, comprising the steps of:

adhereing to the understructure a thin layer of a partially cured emulsion of a polymerizable silicone compound and an inert paste; adhering fibers to the exposed surface of the emulsion;

coating the emulsion with a liquid outer layer that binds with the fibers when dried; and drying the coated emulsion surface layer.

8. The method of claim 7, wherein the silicone compound contains from about 4 to about 6 volumes of a of low viscosity silicone fluid for each volume of a room temperature vulcanizing silicone rubber.

9. The method of claim 8, wherein the emulsion further includes a high viscosity silicone fluid.

10. The method of claim 9, wherein the emulsion and the fibers are adhered with a silicone adhesive containing from about 4 to about 6 volumes of the low viscosity silicone fluid for each volume of the room temperature vulcanizing silicone rubber.

11. The method of claim 7, further comprising the step of forming a skeletal member in the understructure with a composition of latex and talc prior to the adhesion of the emulsion.

* * * * *